United States Patent [19]
Yasushi et al.

[11] Patent Number: 5,613,498
[45] Date of Patent: Mar. 25, 1997

[54] APPARATUS AND METHOD FOR LEADING HUMAN MIND AND BODY

[75] Inventors: Mitsuo Yasushi; Kazuhiro Akiyama; Hiroshi Sato, all of Kawagoe, Japan

[73] Assignee: Pioneer Electronic Corporation, Tokyo, Japan

[21] Appl. No.: 281,728

[22] Filed: Jul. 28, 1994

[30] Foreign Application Priority Data

Aug. 12, 1993 [JP] Japan .................................. 5-200884

[51] Int. Cl.$^6$ ................................................. A61M 21/00
[52] U.S. Cl. ............................................. 128/731; 600/27
[58] Field of Search ...................... 128/731, 732, 128/905; 600/26–28; 364/413.04, 413.27

[56] References Cited

FOREIGN PATENT DOCUMENTS

| | | |
|---|---|---|
| 0375106 | 6/1990 | European Pat. Off. . |
| 0437012 | 7/1991 | European Pat. Off. . |
| 2-168932 | 6/1990 | Japan . |
| 2256276 | 12/1992 | United Kingdom . |

OTHER PUBLICATIONS

Proceedings of IEEE National Aerospace and Electronics Conference, vol. 4, 23 May 1988, pp. 1523–1529, A.M. Junker "Loop–Closure of the Visual–Cortical Response".

Primary Examiner—Angela D. Sykes
Assistant Examiner—Samuel Gilbert
Attorney, Agent, or Firm—Keck, Mahin & Cate

[57] ABSTRACT

An apparatus comprises a separable sensor for detecting physiological data of a human body, a memory for storing the physiological data such as brain waves, skin temperature, and the like detected, a controller for reading out the physiological data from the memory and for supplying to a light modulator, and an LED for emitting a flickering light or a sound converted in accordance with the physiological data toward the user. The physiological data upon leading has been stored in the memory. Therefore, when the same user is intend to lead into the same desired state again, the physiological and mental state of the user which has detected before may be used. There is, consequently, no need to attach a sensor each time of the leading.

12 Claims, 10 Drawing Sheets

APPARATUS AND METHOD FOR LEADING HUMAN MIND AND BODY

BACKGROUND OF THE INVENTION

1. Field of the Invention

This invention relates to an apparatus and method for supplying a leading signal to a human body to lead physiological and mental states of a human being to a desired state, in particular an apparatus and method for leading brain waves by using a pull-in phenomenon of brain waves or the like.

2. Background of the Invention

For example, it is known that there is an intimate relation between the human brain waves and the physiological and mental states. For example, when the human being is in a relax state, many α waves (about 8 to 13 Hz) are included in the human brain waves. When the human being is in an active state, many β waves (about 13 to 30 Hz) are included. When the human being feels sleepiness or the like, many θ waves (about 4 to 8 Hz) are included. Since a pull-in phenomenon such that the human brain waves are tuned with stimuli from the outside occurs in the human brain waves, on the contrary, by tuning the brain waves with stimuli to the human being so as to induce many brain waves in a predetermined frequency band, the human physiological and mental states can be intended to lead a desired state.

For example, Japanese Patent Application No. 63-323698 discloses a brain wave leading apparatus in which an interaction between the human brain waves and the physiological and mental states is used, and by inducing the α waves with stimuli to the body, the human being is led into a relax state, thereby reducing stresses or realizing mental concentration.

In the above brain wave leading apparatus, a sensor to detect the brain waves of a subject, an organism amplifier, a band pass filter, and a light stimulus apparatuses such as an LED for emitting a optical signal or the like are sequentially connected. Furthermore, by fetching the subject into a closed loop, a kind of oscillating circuit is constructed. In an apparatus, the brain waves of the subject are detected, then a band pass filter transmits only the frequency component corresponding to the brain wave to be induced in the detected brain waves. The LED converts the filtered frequency component into the optical signal. The optical signal is, further, fed back as a body stimulus signal to the subject, so that only the signal component corresponding to the predetermined brain wave is circulated in the oscillating circuit. In this manner, the brain waves are led to a desired state by the pull-in phenomenon of the circulating signal.

In the brain wave leading apparatus with the above construction, however, when the brain waves are intended to lead, it is necessary to measure the brain waves of the subject, so that the sensor for detection of the brain waves must be attached and its usage is troublesome.

It is an object of the invention to provide an improved mind and body leading apparatus and method, which is suitable for the repetitive use and which can be easily used.

It is another object of the invention to provide a body leading apparatus in which there is no need to attach a sensor during the leading of the brain waves.

It is further another object of the invention to provide a body leading apparatus of a simple construction.

SUMMARY OF THE INVENTION

According to the invention, there is provided an apparatus comprising: renewable memory means for storing physiological data indicative of a physiological state of the body; and signal producing means for producing a physical/mental leading signal in accordance with physiological data stored in the memory means, wherein the physical/mental leading signal is supplied to the user.

According to the invention, the physical/mental leading signal is produced by the signal producing means based on the physiological data indicative of physiological state of a user or a subject which has previously been stored in the memory means. The produced physical/mental leading signal is then supplied to the user of the apparatus.

According to the invention, when the user is intend to be led to desired physiological and mental states, the physical/mental leading signal is produced based on the prerecorded physiological data indicative of the physical/mental state of the user and including data before and after having led the physical/mental state of the user to the desired state. The produced signal is then supplied to the user, so that the user can be easily promptly led to the desired state. Since the number of parts which are required for leading is small, the apparatus can be easily moved in accordance with the state to be led or a taste of the user. It is possible to efficiently perform the leading to the physiological and mental states in accordance with the taste of the user or the state to be induced.

Further other features and advantages of the present invention will now be clarified referring to the detailed description of the following preferred embodiments with the accompanying drawings.

DETAILED DESCRIPTION OF THE PREFERRED EMBODIMENTS

Figure 1:
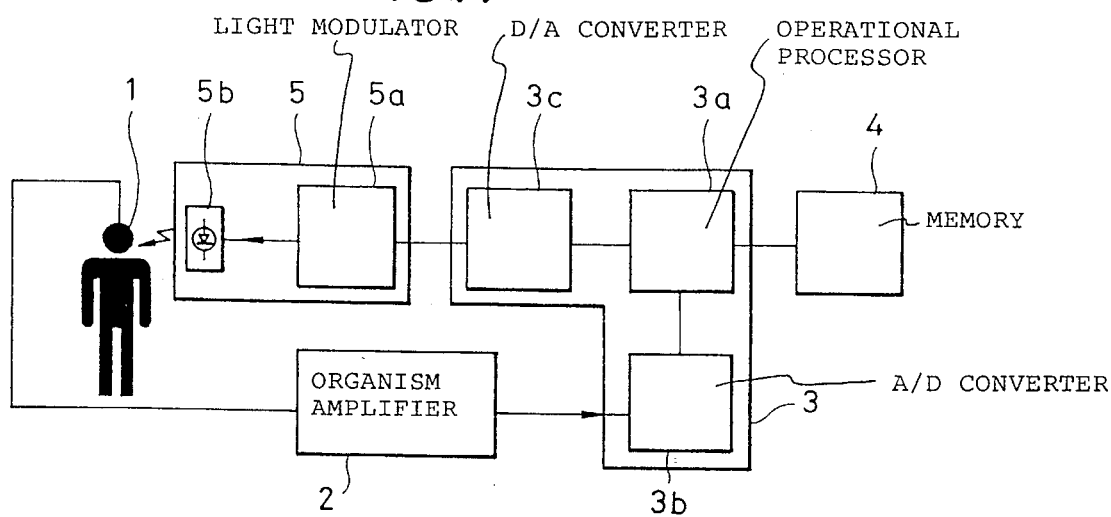
FIG. 1 is a block diagram showing one embodiment of a brain wave leading apparatus according to the present invention.

FIG. 1 shows a brain wave leading apparatus according to the present invention.

Referring to FIG. 1, the brain wave leading apparatus consists of a sensor 1, an organism amplifier 2, a controller 3, a memory 4, and a mind/body leading signal generator 5, each of which is connected each other with this order. The sensor 1 detects a physiological state of each portion of the body of a subject such as human brain waves, skin temperature, or the like as physiological data. In case of detecting the brain waves, a sensor is attached to the head portion. In case of detecting a skin potential, skin vibration, skin resistance, or the like, a sensor is attached to the wrist or the like. Namely, a sensor suitable for detection of each physiological state is attached to each associated portion of the body. The organism amplifier 2 amplifies a signal detected by the sensor to a predetermined level.

The memory 4 stores the physiological data and comprises a RAM, a IC card, a floppy disk, or the like and constructs memory means together with the controller 3. The mind/body leading signal generator 5 functions as signal producing means and generates a flickering light as a mind/body leading signal toward the user of the apparatus. In case of using the flickering light as a mind/body leading signal, the mind/body leading signal generator 5 comprises a light modulator 5a connected to the controller 3 and an LED 5b placed directly in front of the eyes of the subject. The generator 5 converts an input signal into the flickering light to supply to the subject.

The controller 3 includes an operational processor 3a to perform a digital process, an A/D converter 3b for converting an analog signal into a digital signal at its input, and a D/A converter 3c for converting a digital signal into a analog signal at its output. The operation processor 3a executes an arithmetic operation such as calculation of an instantaneous frequency and amplitude of the brain waves, an average amplitude and a weighted mean of the frequency, and detection of a temperature difference of the skin temperatures, or the like. The operational processor 3a also executes an arithmetic operation to gain control an output level of the controller 3. The operational processor 3a also controls the writing and reading operations for the memory 4. The controller 3 further has a switch (not shown) which may be operated by the user. The switch is means which is turned on or off at the time of the start and end of sleep of the subject or depending on the relax state and notifies the condition of the subject to the controller 3.

The above brain wave leading apparatus is formed separably at a connecting point between the organism amplifier 2 and the controller 3.

The operation of the apparatus will now be described hereinafter.

Figure 2:
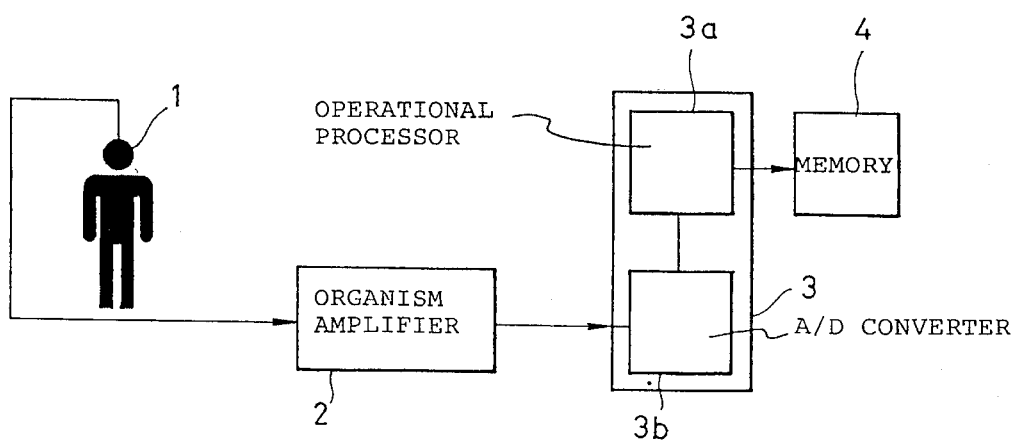
FIG. 2 is a block diagram for detecting and recording physiological data in the apparatus of FIG. 1.

A method of recording a physiological state will now be described with reference to FIG. 2. Physiological data recorded are date such the brain wave at the times of the start and end of the sleep or in the relax state or respiratory state, electrocardiogram, and the like. It is well known that the brain waves directly have the intimate relation with the human physiological and mental states. In place of the brain waves, physiological phenomena such as skin potential, skin vibration, skin resistance, respiratory waves and etc. having predetermined correlations with the brain waves can be also recorded as physiological data.

When the corresponding sensor 1 is attached to each portion of the body associated with each physiological data and an instruction to start the recording is generated, the controller 3 starts the detection of the physiological data. The detected physiological data is sent to the operational processor 3a through the organism amplifier 2. In association with the above operation, the latest physiological data is sequentially supplied to the memory 4. The data supply to the memory 4 is continued until either an instruction to finish the recording or an instruction to stop the recording is received.

A recording method of the physiological data when the subject is intend to lead into a relax condition will be first described. For example, as a method of recording the physiological data when the subject is intend to lead into the relax state, there are four methods for relaxation which will be explained hereinafter.

Figure 3:
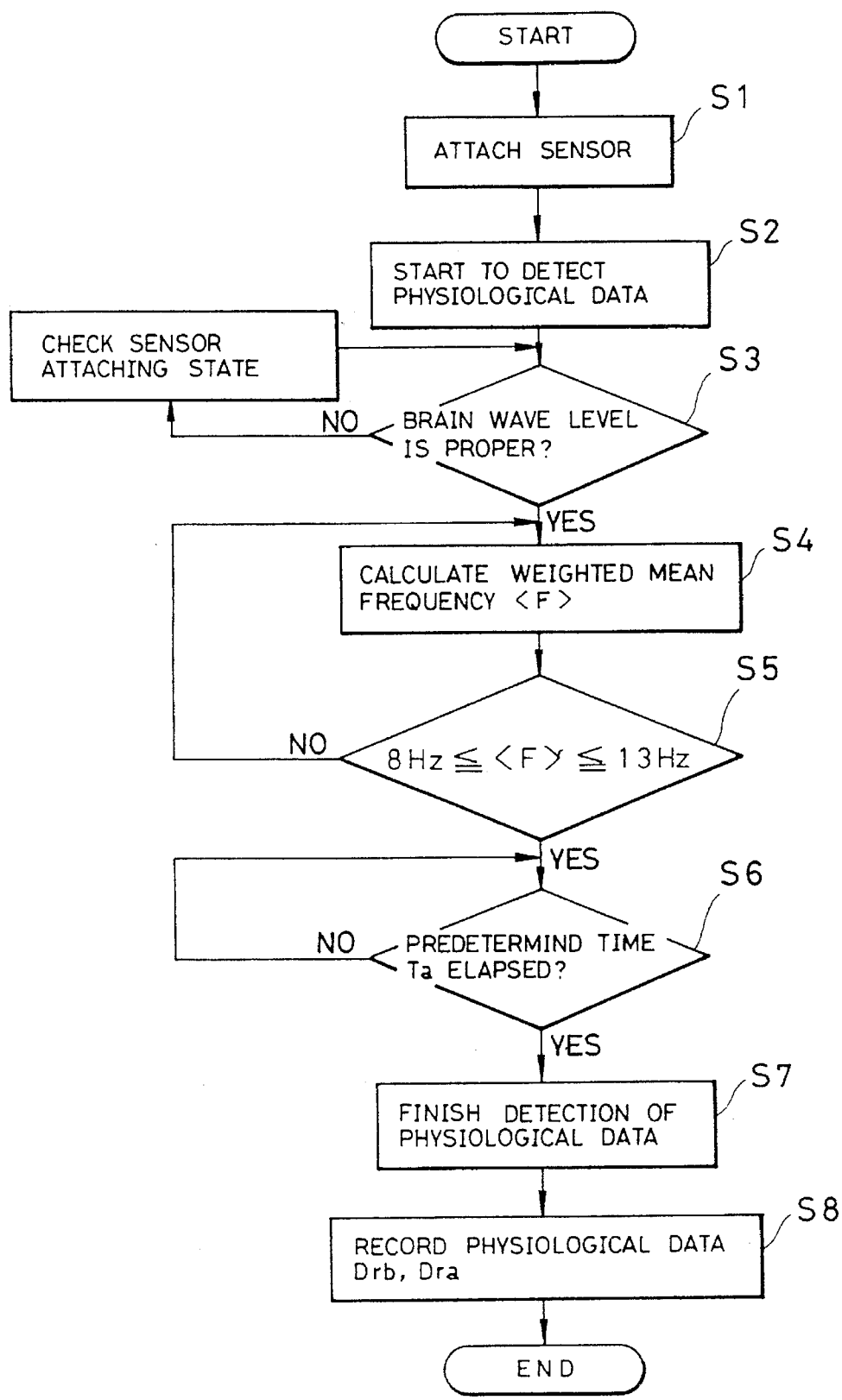
FIG. 3 is a flow diagram illustrating one algorithm for recording physiological data when the subject is intended to lead a relax state.

A first method for recording data for relaxation is characterized in that the physiological data is recorded in view of a relax state of the body based on a weighted mean frequency <F> of the brain waves. For example, as shown in FIG. 3, various kinds of sensors are attached to the associated portion of the body and the detection is started (steps 1 and 2). A check is made to see if the brain wave sensor is detected the brain waves correctly or not (step 3). In the operational processor 3a, the weighted mean frequency <F> of the brain waves is always calculated (step 4). When it is determined that the weighted mean frequency <F> enters within frequency band corresponding to the relax state, namely, an α wave region of 8 to 13 Hz (step 5), this detection time point is set to a reference time point and the detection of the physiological data is continued until a predetermined time period Ta has passed, and then the detection is finished (steps 6 and 7). Physiological data Drb and Dra which were measured during a predetermined time period Tb before the reference time point and during a predetermined time period Ta after the reference time point are respectively stored in the memory as physiological data before/after the state of the subject being led to the relax state (step 8). Now, assuming that an instantaneous frequency is set to Fi and an instantaneous amplitude is set to Ai, the weighted mean frequency <F> of the brain waves is defined by the following equation (1).

$$<F> = \sum_i (F_i - (A_i)^2) / \sum_i (A_i)^2 \qquad (1)$$

Figure 4:
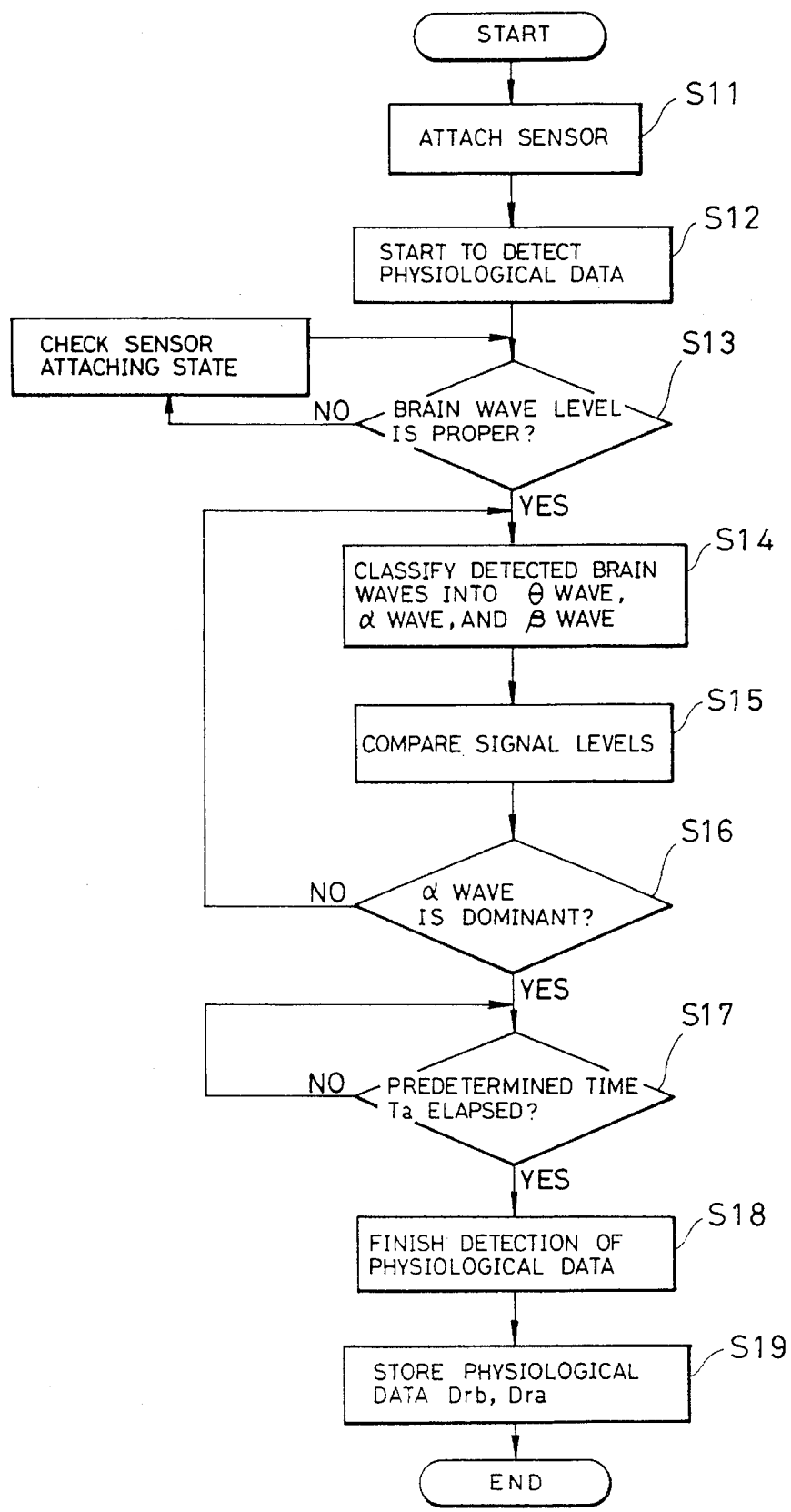
FIG. 4 is a flow diagram illustrating another algorithm for recording physiological data when the subject is intended to lead a relax state.

A second method for recording data for relaxation is characterized in that the physiological data is recorded in view of the relax state of the body based on the detected signal levels in the three bands of the θ wave (4 to 8 Hz), α wave (8 to 13 Hz), and β wave (13 to 30 Hz) of the brain waves. According to the second method, as shown in FIG. 4, various kinds of sensors are attached to the associated portions of the body and the detection of the physiological data is started (steps 11 and 12). A check is made to see if the brain wave sensor has detected the brain waves correctly or not (step 13). The detected brain waves in the physiological data are classified into three bands of the θ wave, α wave, and β wave by filters (not shown) (step 14). The signal levels of the respective bands are mutually compared at the operational processor 3a (step 15). After the start of the detection of the brain waves, when the signal level of the α wave becomes dominant, that is, when a state in which the signal level of the α wave has a level of a predetermined ratio or more as compared with those of the signal levels of the other two bands has continued for a predetermined time period or longer (step 16), this time point is set to the reference time point and the detection of the physiological data is further continued until a predetermined time period Ta has passed from the reference time point. After the predetermined time period Ta the detection is finished (steps 17 and 18). The physiological data Drb and Dra measured during the predetermined time periods Tb and Ta before and after the reference time point are respectively stored in the memory as physiological data before and after the state of the subject being led to the relax state (step 19).

A third method for recording data for relaxation is characterized in that the physiological data is recorded in view of the relax state of the body based on the distribution of the skin temperatures of the respective portions of the body. The determination of reaching the relax state by the distribution of the skin temperatures is performed in the following manner. Namely, the skin temperature of a portion such as a finger tip is easily mentally influenced, and the temperature of the portion such as inside of an external ear or armpit is relatively stable, so that both of them are compared. When a difference between both temperatures is equal to or lower than a predetermined level, it is concluded that the subject entered the relax state.

Figure 5:
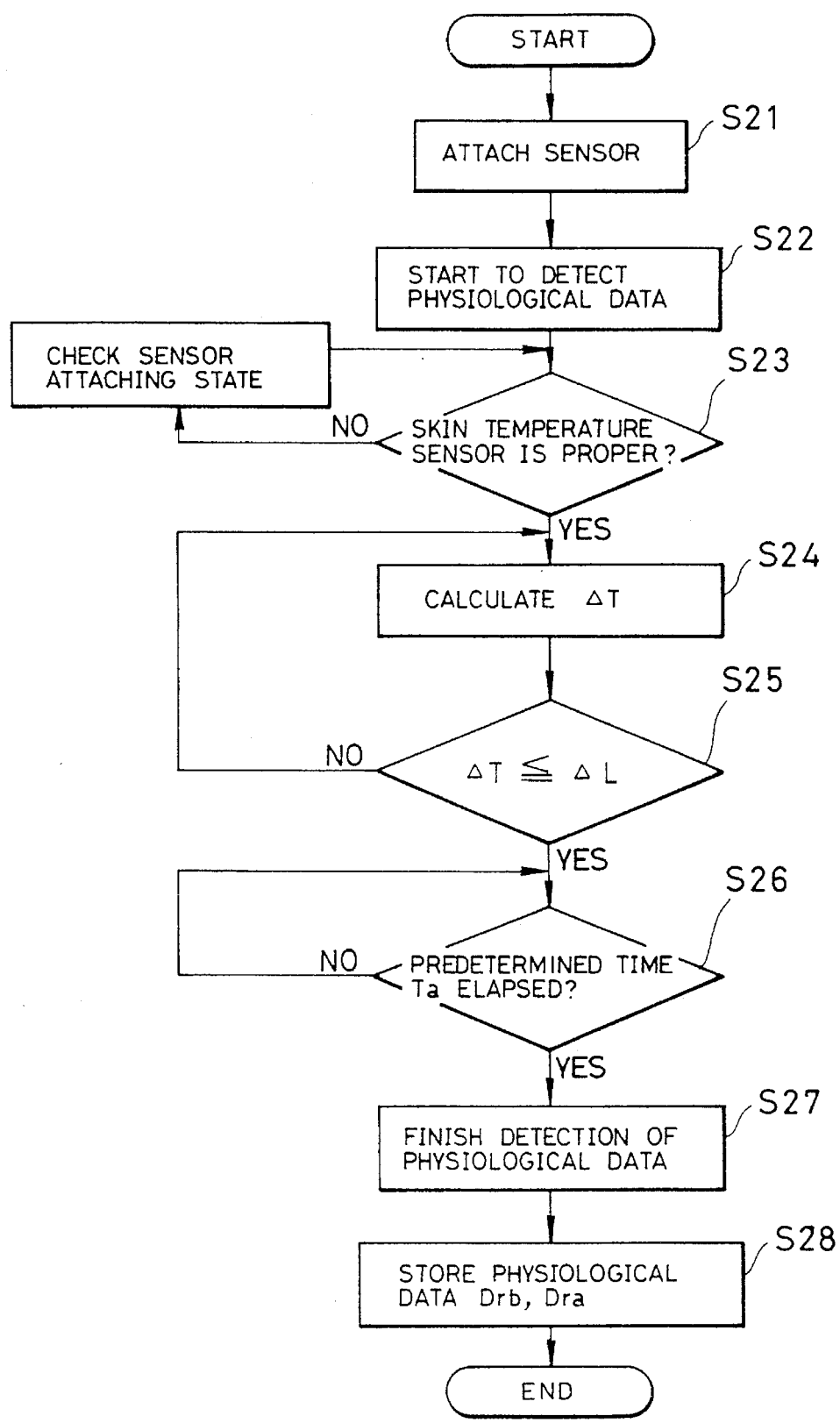
FIG. 5 is a flow diagram illustrating still another algorithm for recording physiological data when the subject is intended to lead a relax state.

As shown in FIG. 5, according to the above third method, various kinds of sensors are attached to the associated portions of the body and the detection of the physiological data is started (steps 21 and 22). A check is made to see if the skin temperature sensors attached to the finger tip and the armpit have detected skin temperatures Tf and Ts correctly (step 23). The operational processor calculates a temperature difference ΔT between the skin temperature Tf of the finger tip and the skin temperature Ts of the armpit (step 24). When the temperature difference ΔT is equal to or less than a predetermined level ΔL (step 25), this time point is set to a reference and the detection of the physiological data is continued until the predetermined time period Ta has passed. After that, the detection is finished (steps 26 and 27). The physiological data Drb and Dra which were measured at the predetermined time periods Tb and Ta before and after the reference time point are respectively stored in the memory as physiological data before and after the state of the subject being led to the relax state (step 28).

Figure 6:
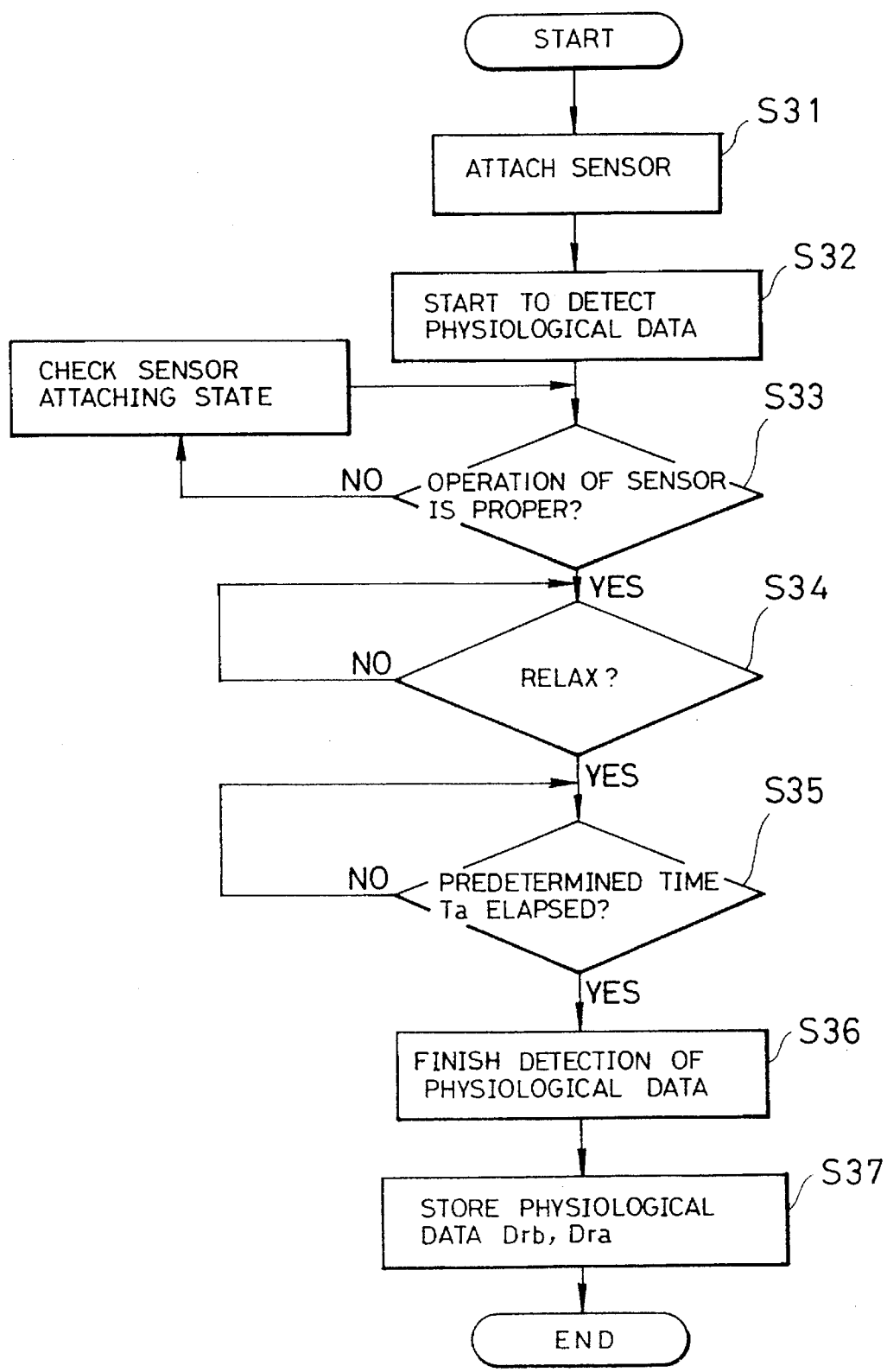
FIG. 6 is a flow diagram illustrating yet another algorithm for recording physiological data when the subject is intended to lead a relax state.

A forth method for recording data for relaxation is characterized in that the physiological data is recorded by the subject attached with the sensors in view of the his relax state. As shown in FIG. 6, according to the fourth method, various sensors are attached to the portions of the body and the detection of the physiological data is started (steps 31 and 32). A check is made to see if each sensor has detected the data (step 33) correctly. When the subject himself concludes that he is led into a relax state (step 34), the time point of such a conclusion is set to a reference and the detection of the physiological data is continued until the predetermined time period Ta has passed. After that, the detection is finished (steps 35 and 36). The physiological data Drb and Dra which were measured at the predetermined time periods Tb and Ta before and after the reference time point are respectively stored in the memory as physiological data before and after the state of the subject being led to the relax state (step 37).

A method for recording physiological data for starting a sleep will now be described. As a method of recording physiological data at the start of the sleep, there are three methods as will be explained hereinbelow.

A first method for recording physiological data for starting a sleep is characterized in that falling to sleep of the subject is detected and the physiological data before and after the start of the sleep is recorded as physiological data at the start of the sleep. As a sensor to detect that the subject falls into the sleeping state, for example, the apparatus provides a switch connected to the controller by a wired or wireless manner and being able to be gripped by the subject. For example, the grasping power of the subject turns on the switch. when the grasping power is reduced to zero, the switch is turned off. The switch is not limited to the above construction but can have a proper construction so long as it can detect the start of the sleep of the subject.

Figure 7:
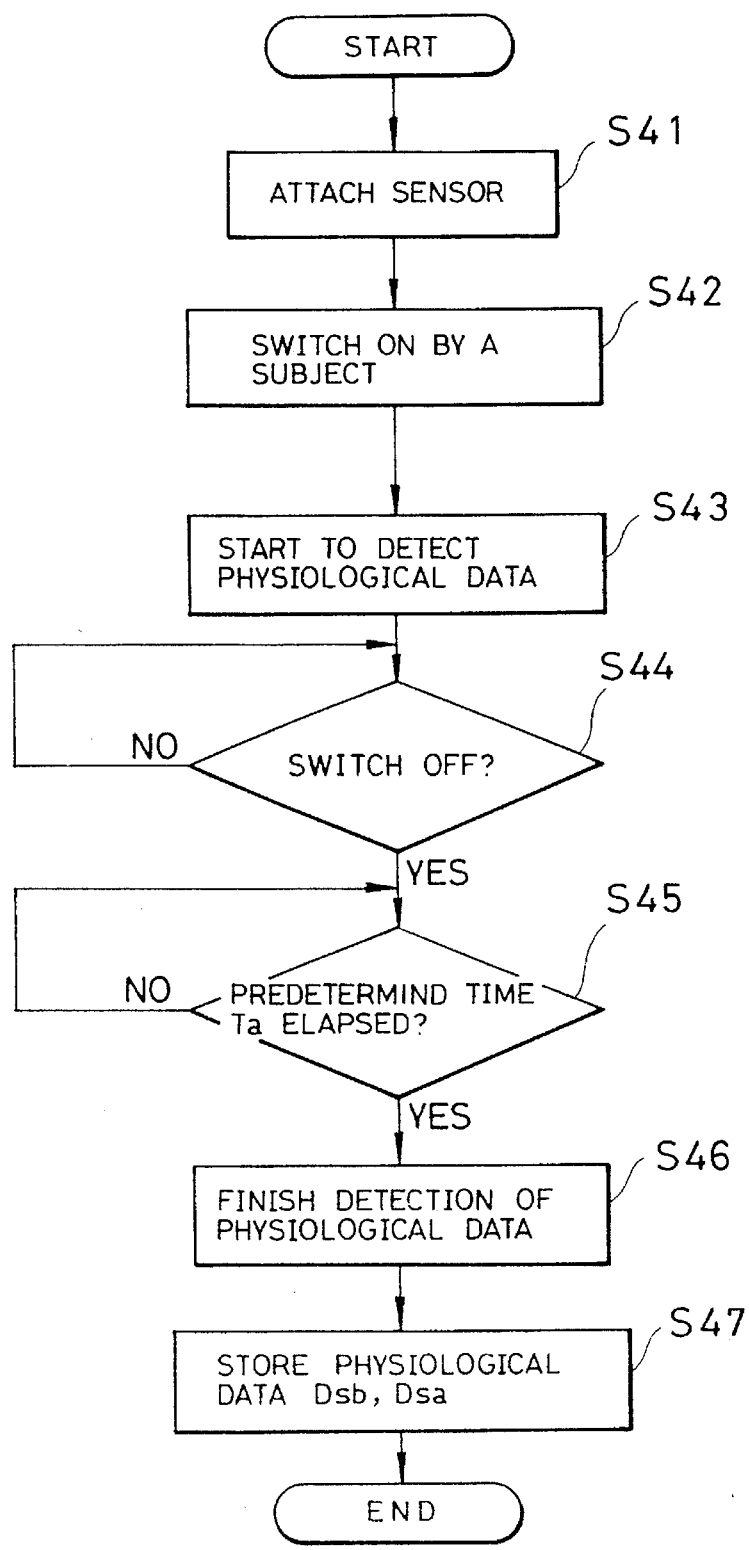
FIG. 7 is a flow diagram illustrating one algorithm for recording physiological data when the subject starts to sleep.

As shown in FIG. 7, according to the above first method, the subject attached with the sensors is promoted to sleep with grasping the switch (steps 41 and 42). The recording of the physiological data is started (step 43). Since this method is performed on the assumption that the subject continuously grasps the switch for a period during which he has a consciousness. When the subject falls into sleep, no grasping power acts and then the switch is turned off (step 44). The instance at which the action of the grasping power is reduced to zero, it is set to a reference time point and the physiological data is detected until the predetermined time period Ta has passed (steps 45 and 46). The physiological data measured at the predetermined time periods Tb and Ta before and after the reference time point are respectively stored in the memory as physiological data Dsb and Dsa before and after the start of the sleep (step 47).

Figure 8:
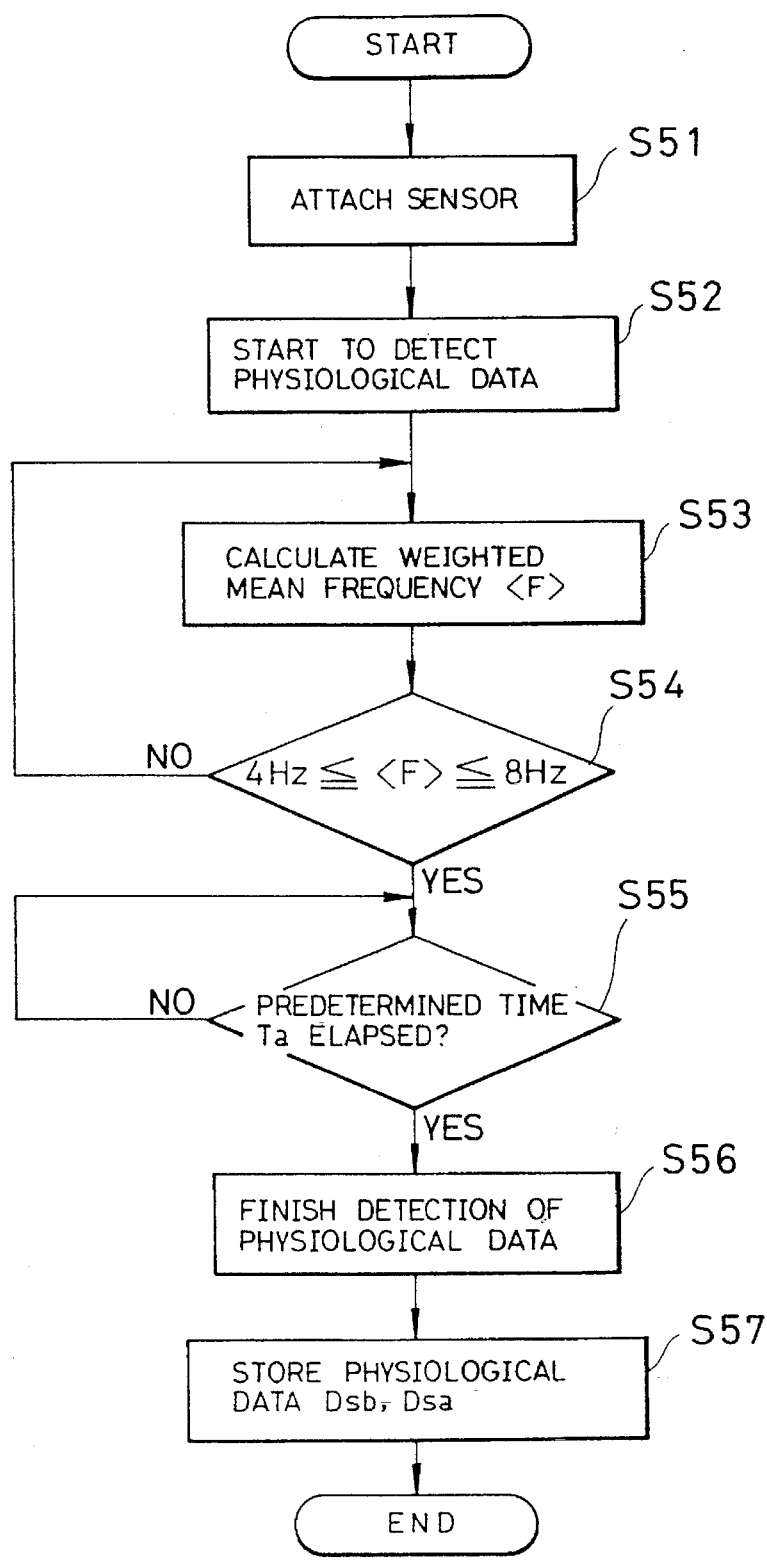
FIG. 8 is a flow diagram illustrating another algorithm for recording physiological data when the subject starts to sleep.

A second method for recording data for starting sleep is characterized in that the physiological data is recorded with determining the sleep-starting point of the subject in view of the weighted mean frequency <F> of the brain waves. According to the second method, for example, as shown in FIG. 8, various kinds of sensors are attached to the associated portions of the body and the detection of the physiological data is started (steps 51 and 52). Subsequently, the operational processor 3a always calculates the weighted mean frequency <F> of the detected brain waves as the physiological data (step 53). When a time point when the weighted mean frequency <F> has led within the frequency band corresponding to the sleeping state, namely, the region of the θ wave of 4 to 8 Hz is detected for recording physiological data for starting a sleep (step 54). This time point is set to a reference time point, and the detection of the physiological data is continued until the predetermined time period Ta from the reference has passed. After that, the detection is finished (steps 55 and 56). The physiological data measured at the predetermined time periods Tb and Ta before and after the start of the sleep are respectively stored in the memory as physiological data Dsb and Dsa before and after the sleep-starting point (step 57).

Figure 9:
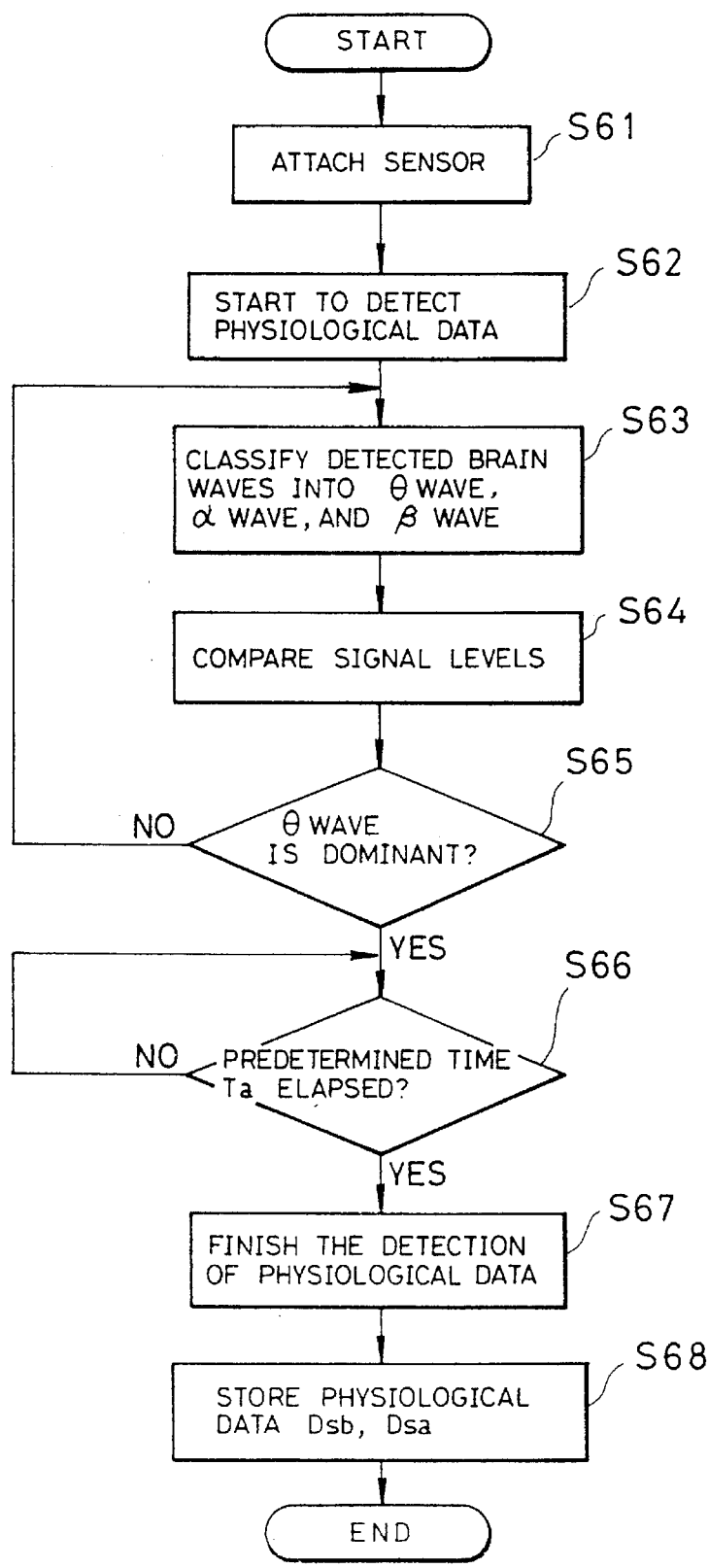
FIG. 9 is a flow diagram illustrating still another algorithm for recording physiological data when the subject starts to sleep.

A third method for recording data for starting sleep is characterized in that the physiological data is recorded with determining the sleep-starting time point of the subject in view of the detected signal levels of the three bands of the θ wave (4 to 8 Hz), α wave (8 to 13 Hz), and D wave (13 to 30 Hz) of the brain waves. According to the third method, as shown in FIG. 9, various kinds of sensors are attached to the associated portions of the body and the detection of the physiological data is started (steps 61 and 62). The detected brain waves in the physiological data are classified into three bands of the θ wave, α wave, and β wave by filters (not shown) in the controller 3 (step 63). the operational processor 3a compares each of the signal levels of the three bands mutually (step 64). When it is concluded that the signal level of the θ wave became dominant, that is, the signal level of the θ wave has a upper level of a predetermined ratio as compared with those of the signal levels of the other two bands during a predetermined time period (step 65), this time point of the conclusion is set to a reference point and the detection of the physiological data is continued until the predetermined time Ta has passed (steps 66 and 67). The physiological data measured at the predetermined time periods before and after the reference time point are respectively stored in the memory as physiological data Dsb and Dsa before and after the start of the sleep (step 68).

Figure 10:
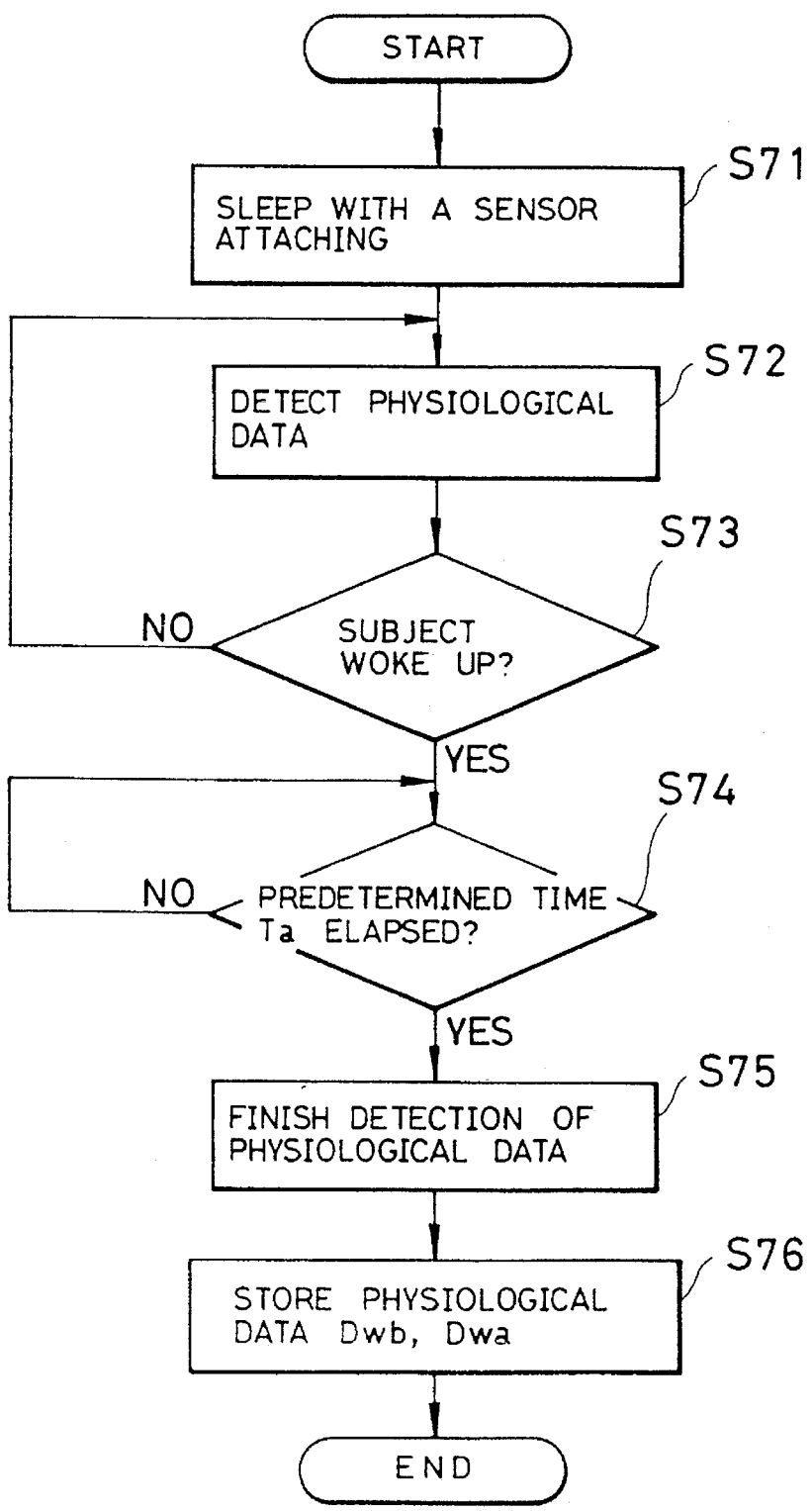
FIG. 10 is a flow diagram illustrating one algorithm for recording physiological data when the subject wakes up.

A method for recording physiological data at the end of the sleep, namely, when the subject wakes up will now be described. As a sensor to detect that the subject waked up, for example, the apparatus provides a switch connected to the controller 3 in a wired or wireless manner and being able to operate by the subject. As shown in FIG. 10, the subject is intend to sleep with sensors attached for detection of physiological data and the physiological data is also detected even during the sleeping period (steps 71 and 72). For example, the subject presses the switch just after he waked up, thereby transmits an information of his waking up to controller 3 (step 73). The time point when the subject wakes up is set to a reference time point and the detection of the physiological data is further continued until the predetermined time period Ta has passed (steps 74 and 75). The physiological data measured during the predetermined time periods Tb and Ta before and after the reference time point is respectively stored in the memory as physiological data Dwb and Dwa before and after the end of the sleep (step 76).

As mentioned above, the physiological data corresponding to the relax state, the sleep-starting, and the end of the sleep is respectively obtained and stored in the memory by the above methods. Further, when recording the physiological data corresponding to the relax state, the start of the sleep, and the end of the sleep, by recording the physiological data while supplying the body leading signals corresponding to the respective states to the subject, desired physiological data can be further easily obtained.

When recording the physiological data corresponding to each state by the above methods, if a state in which the subject doesn't reach each state cannot be detected, a message indicating such a fact is displayed by the controller 3. For preparation of the case where the physiological data corresponding to each state cannot be recorded, therefore, the physiological data which was statistically processed may be possessed. These data are such that a general person reaches the relax state or falls into sleep or wakes up, and which can be also previously stored as standard data in the memory. The standard data can be also used when a subject is set to the user of the apparatus and then the brain waves are led without previously recording the physiological data corresponding to each state of the subject.

Although each of the above methods uses a construction such that after completion of the detection, the physiological data corresponding to each state is stored in the memory in a lump, the present invention is not limited to such a construction but the physiological data can be also stored into the recording section at the same time of detecting itself.

Figure 11:
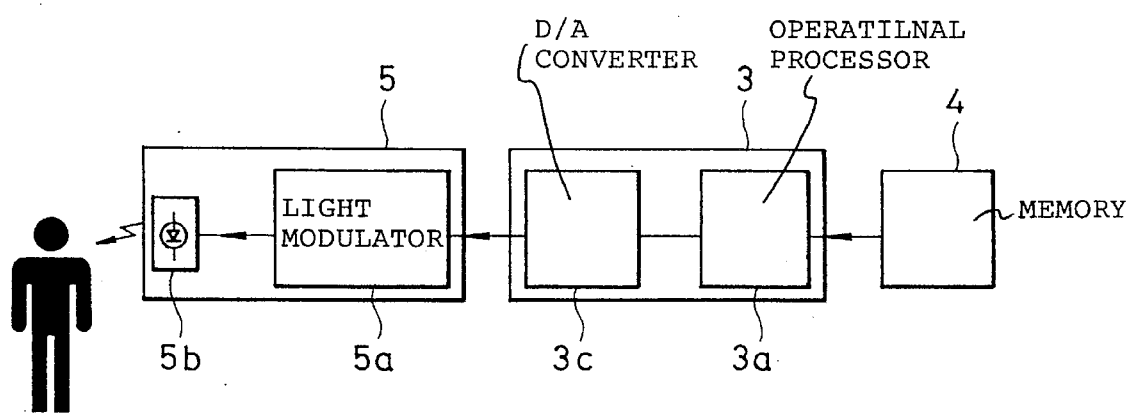
FIG. 11 is a block diagram for leading brain waves based on the associated physiological data in the apparatus shown in FIG. 1.

A method for leading the brain waves of the user into a desired state by using the physiological data recorded in the memory will now be described. In this case, as shown in FIG. 11, the corresponding physiological data is read out from the memory 4 and is supplied to the body leading signal generator 5. The flickering light generated from the body leading signal generator 5 is supplied to the user. When the brain waves are led, since there is no need to detect the physiological data of the user, the sensor 1 and the organism amplifier 2 may be separate from the apparatus, so that the apparatus may reduce its weight.

A case of leading the brain waves of the user into the relax state or the sleep start state will be first described. The physiological data (Drb and Dra) or (Dsb and Dsa) corresponding to the relax state or the sleep start state recorded by the above methods are read out from the memory 4 and is converted into the light signals by the body leading signal generator. As a method of deciding the order of the physiological data supplied to the user, there are the six methods explained hereinlater according to the state or taste of the user.

A first method for leading the user into the relax state includes supplying the light based on the physiological data Drb and then the light based on the physiological data Dra to the user once respectively. Similarly, in case of leading the user into the sleeping state, the light based on the physiological data Drb is once supplied to the user and then the light based on the physiological data Dra is once supplied to the user.

A second method for leading the user into relax state includes supplying the light based on the physiological data Drb and the light based on the physiological data Dra alternately to the user until the user has been led into the relax state. Similarly, the light based on the physiological data Dsb and the light based on the physiological data Dsa are alternately supplied to the user until the user has fallen into sleep. After that, the apparatus is manually or automatically stopped.

A third method for leading the user to a relax state includes supplying the light based on the physiological data Drb to the user and after that supplying the light based on the physiological data Dra repetitively to the user until the user is led into the relax state. In case of leading the user into the sleeping state, the light based on the physiological data Dsb is first supplied to the user and then the light based on the physiological data Dsa is repetitively supplied to the user until the user is led into the sleeping state. That is, after the lights based on the physiological data Drb and Dsb before the user reached the relax state or the sleeping state was supplied to the user, only the lights based on the physiological data Dra and Dsa after the user reached the relax state or sleeping state are supplied to the user, thereby leading the brain waves of the user into a desired state. After the user reached the relax state or the sleeping state, the apparatus is manually or automatically stopped.

When leading the user into the relax state, the light based on the physiological data Drb is first supplied to the user and the lights based on the latter half portion of the physiological data Drb and the former half portion of the physiological data Dra are subsequently alternately supplied to the user, thereby leading the brain waves of the user into the relax state. That is, the lights based on the physiological data Drb and Dra before and after the reference time point when it is concluded that the user has reached the relax state are supplied to the user, thereby leading the brain waves of the user into a desired state. A ratio at which the data is selected as a latter half portion from the physiological data Drb and the data is selected as a former half portion from the physiological data Dra can be properly set depending on the taste or state of the user. When leading the user into the sleeping state, it is sufficient to use the physiological data Dsb in place of the physiological data Drb and to use the physiological data Dsa in place of the physiological data Dra and to execute the operations in a manner similar to the case of the relax state. After the user reached the relax state or sleeping state, the apparatus is manually or automatically stopped.

When leading the user into the relax state, the light based on the latter half portion of the physiological data Drb and the light based on the former half portion of the physiological data Dra are alternately supplied to the user, thereby leading the user into the relax state. That is, the lights based on the physiological data Drb and Dra before and after the reference time point when the user has reached the relax state are supplied to the user, thereby leading the user into a desired state. A ratio at which the data is selected as a latter half portion from the physiological data Drb and the data is selected as a former half portion from the physiological data Dra can be properly set depending on the taste or state of the user. When leading the user into the sleeping state, it is sufficient to use the physiological data Dsb in place of the physiological data Drb and to use the physiological data Dsa in place of the physiological data Dra and to execute the operations in a manner similar to the case of the relax state. After the user reached the relax state or sleeping state, the apparatus is manually or automatically stopped.

When leading the user into the relax state or sleeping state in an any one of the above first to fifth methods, the sensors are previously attached to the user. The sensor detects that the user has reached the relax state or sleeping state during the leading. The lights based on the physiological data Dra or Dsa recorded from the detection time period, namely, the former half portion of the physiological data after the reference time point is supplied once to the user. The leading operation is finished. When leading the user into the relax state, a fact that the user has reached the relax state is not detected by the sensor but can be also determined by the user by himself.

A case of leading the user into a waking-up state will now be described. The physiological data Dwb and Dwa corresponding to the sleep end state which were recorded by the above method are read out from the memory and converted into the lights by a light emitting section. As a method of deciding the order of the physiological data which is supplied to the user, there are the following four methods as will be explained hereinlater depending on the state of the user. In any one of the methods, the light is supplied to the user for a predetermined time interval during which the user is waken up by manually or by a timer.

The light based on the physiological data Dwb and then the light based on the physiological data Dwa are respectively supplied only once to the user.

The light based on the physiological data Dwb and then the light based on the physiological data Dwa are alternately supplied to the user until the user wakes up. After the user woke up, the apparatus is manually or automatically stopped.

The light based on the physiological data Dwb is first supplied to the user. Subsequently, only the light based on the physiological data Dwa is repetitively supplied until the user wakes up. That is, after the light based on the physiological data Dwb to wake up was supplied to the user, only the light based on the physiological data Dwa after the user woke up is supplied to the user. After the user woke up, the apparatus is manually or automatically stopped.

Only the light based on the physiological data Dwa is repetitively supplied until the user wakes up. That is, only the light based on the physiological data Dwa after he woke up is supplied to the user. After the user woke up, the apparatus is manually or automatically stopped.

To efficiently lead the brain waves of the user into the waking-up state by each of the above methods, any proper means for gradually increasing the light luminance or the like can be used.

When the brain waves of the user are led into a desired state as mentioned above, since they can be led by using the prerecorded physiological data, there is no need to attach the sensor each time of the leading, so that the leading can be easily performed.

Since there is no need to use the sensor to always detect the change in physiological state such as brain waves upon leading, the detecting system such as sensor 1 and organism amplifier 2 and the like can be eliminated from the apparatus during leading. The number of parts required for leading, therefore, is reduced and the apparatus can be easily moved. The brain waves can be easily led in accordance with the state of the user at a desired location of the user. The brain waves, consequently, can be effectively led.

The apparatus can be also commonly used by a plurality of users. In this case, the ID data of each person is stored into the memory together with the physiological data of each person. In case of leading a user, the physiological data of the corresponding person is read out on the basis of the ID data and leading of the brain waves is started. When leading without previously recording the physiological data of each person, it is sufficient to read out the standard data from the memory and to perform the leading.

As a body leading signal, an leading signal such as sound, electricity, vibration, or the like can be also used in place of the signal disclosed in the above embodiments. In case of using the sound as a body leading signal, a sound source is arranged at a position near the ear. In case of using an electric stimulus or a vibration stimulus as a body leading signal, a vibrator or a stimulator is arranged at a predetermined position of the body such as a wrist. In the above embodiments, although the light emitted from the LED has been used as a body leading signal, in case of using the light as a body leading signal, it may be also possible to use a desk lamp or a room lamp by flickering it.

Although the apparatus of each of the embodiments has been constructed so that the apparatus processes the physiological data as digital data, the invention is not limited to such a construction. Even by constructing so as to process the physiological data as analog data, operations and effects similar to those of the above embodiments can be also obtained.

The case where the brain waves are directly detected and the brain waves are led has been described above in each of the embodiments of the invention. The invention, however, is not limited to the brain waves but even if any one of the skin potential, skin vibration, skin resistance, respiratory state, and electrocardiogram each having a predetermined correlation with the brain waves is used, the human mental and physiological states can be led to a desired state. For example, an autonomic training such as a respiratory training or the like by using a respiratory wave indicative of the respiratory state can be also executed.

What is claimed is:

1. An apparatus for supplying a physical/mental leading signal to a user to lead a physiological condition of the user to a desired state, comprising:

renewable memory means storing physiological data indicative of a physiological condition of the user or a subject, said physiological data having previously been detected from the user during a period in which a physiological state of the user has led to a desired state;

signal producing means for producing a physical/mental leading signal for the user or subject, based on the physiological data stored in said memory means; and controller connected to both of said memory means and said signal producing means, for controlling said memory means and said signal producing means.

2. An apparatus according to claim 1, wherein said physical/mental leading signal has a frequency for leading a physical/mental condition of the user into a desired physical/mental state.

3. An apparatus according to claim 1, further comprising detecting means connected to said controller, for detecting said physiological data, wherein said memory means stores an output supplied from said detecting means and said detecting means is disconnectable from the controller during a time period in which the physical/mental leading signal is supplied to the user.

4. An apparatus according to claim 1, wherein said physical/mental leading signal comprises a light which flickers in accordance with said physiological data.

5. An apparatus according to claim 1, wherein said physical/mental leading signal comprises a sound having a frequency in accordance with said physiological data.

6. An apparatus for supplying a physical/mental leading signal to a user to lead a physiological or mental state of the user into a desired physiological or mental state, comprising:

renewable memory means storing physiological data indicative of a physiological state of a subject, said data having previously been detected from the user during a period in which a physiological state of the user has led to a desired state, said data including two different kinds of data, one being a group of data during a predetermined period just before the physiological or mental state of the user is led to the desired physiological or mental state, and the other being a group of data during a second predetermined period just after the user has acquired the desired physiological or mental state;

signal producing means for producing a physical/mental leading signal sequentially based on said physiological data stored in said memory means; and controller connected to both of said memory means and said signal producing means, for controlling said memory means and skid signal producing means.

7. An apparatus according to claim 6, wherein said physical/mental leading signal has a frequency corresponding to said desired physical/mental state into which the user is led.

8. An apparatus according to claim 6, further comprising detecting means connected to said controller, for detecting said physiological data, wherein said memory means stores an output supplied from said detecting means and said detecting means is disconnectable from the controller during a time period in which said physical/mental leading signal is supplied to the user.

9. An apparatus according to claim 6, wherein said physical/mental leading signal comprises a light which flickers in accordance with said physiological data.

10. An apparatus according to claim 6, wherein said physical/mental leading signal comprises a sound having a frequency in accordance with said physiological data.

11. An apparatus for supplying a physical/mental leading signal to a user to lead a physiological or mental state of the user into a desired physiological or mental state, comprising:

separable detecting means for detecting physiological data indicative of a physiological or mental state of the user when the physiological or mental state of the user is led into the desired physiological or mental state;

memory means for storing physiological data, said data including two different kinds of data, one being a group of data during a first predetermined period just before the physiological or mental state of the user is led to the desired physiological or mental state, and the other being a group of data during a second predetermined period just after the user has acquired the desired physiological or mental state;

signal producing means for producing a physical/mental leading signal sequentially in accordance with the physiological data stored in said memory means; and controller connected to each of the detecting means the memory means, and the signal producing means for the controlling thereof, wherein said detecting means is disconnectable from the controller during a time period in which the memory means includes the physiological data.

12. A method for supplying a physical/mental leading signal to a user to lead a physiological or mental state of the user into a desired physiological or mental state, comprising:

detecting and storing physiological data indicative of the physiological and mental state of the user, the stored data including two different kinds of data, one being a group of data during a first predetermined period just before the physiological or mental state of the user is led into the desired state, and the other being a group of data during a second predetermined period just after the user has acquired the desired physiological or mental state;

producing a physical/mental leading signal in accordance with the physiological data stored; and supplying the physical/mental leading signal produced to the user.

* * * * *